United States Patent
Fukutani

(10) Patent No.: US 9,883,807 B2
(45) Date of Patent: Feb. 6, 2018

(54) OBJECT INFORMATION ACQUIRING APPARATUS AND CONTROL METHOD THEREFOR

(71) Applicant: CANON KABUSHIKI KAISHA, Tokyo (JP)

(72) Inventor: Kazuhiko Fukutani, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 940 days.

(21) Appl. No.: 14/171,890

(22) Filed: Feb. 4, 2014

(65) Prior Publication Data

US 2014/0235993 A1 Aug. 21, 2014

(30) Foreign Application Priority Data

Feb. 19, 2013 (JP) .................. 2013-030145

(51) Int. Cl.
*A61B 5/00* (2006.01)
(52) U.S. Cl.
CPC .......... *A61B 5/0095* (2013.01); *A61B 5/4312* (2013.01)
(58) Field of Classification Search
CPC combination set(s) only.
See application file for complete search history.

(56) References Cited

U.S. PATENT DOCUMENTS

| | | | |
|---|---|---|---|
| 8,687,868 B2 | 4/2014 | Fukutani et al. | 382/128 |
| 2010/0087733 A1 | 4/2010 | Nakajima et al. | 600/437 |
| 2010/0331662 A1 | 12/2010 | Fukutani et al. | 600/407 |
| 2011/0232385 A1 | 9/2011 | Nanaumi et al. | 73/602 |
| 2012/0243369 A1 | 9/2012 | Sudo et al. | 367/13 |
| 2012/0296192 A1 | 11/2012 | Fukutani | 600/407 |
| 2013/0035570 A1 | 2/2013 | Miyasato | 600/323 |
| 2013/0245420 A1 | 9/2013 | Fukutani | 600/407 |
| 2014/0018659 A1 | 1/2014 | Fukutani | 600/407 |

FOREIGN PATENT DOCUMENTS

CN 102908164 2/2013
WO WO 2012/140865 A 10/2012

OTHER PUBLICATIONS

Sheinfeld et al., "The use of pulse synthesis for optimization of photoacoustic measurements", Optical Society of America, vol. 17, No. 9 / Optics Express, Apr. 27, 2009.*

(Continued)

*Primary Examiner* — Rajeev Siripurapu
*Assistant Examiner* — Farshad Negarestan
(74) *Attorney, Agent, or Firm* — Fitzpatrick, Cella, Harper & Scinto

(57) ABSTRACT

An object information acquiring apparatus includes a probe configured to detect a photoacoustic wave generated from an object irradiated with light, a signal collector configured to generate a first detection signal from the photoacoustic wave, a signal processor configured to generate, from the first detection signal, a second detection signal in which a component having a phase inverted from the phase of a component deriving from the photoacoustic wave is reduced, by using a differential signal of an impulse response of the probe, and an image generator configured to generate image data on the inside of the object using the second detection signal.

11 Claims, 7 Drawing Sheets

(56) References Cited

OTHER PUBLICATIONS

Extended ESR dated Jun. 5, 2014 in counterpart European Patent Application 14152379.5 (in English).
Office Action dated Jun. 23, 2015, in counterpart Chinese (P.R. China) patent application 201410050587.7, with translation.
X. Minghua et al., "Photoacoustic Imaging in Biomedicine", *Review of Scientific Instruments*, vol. 77, 041101 (Apr. 17, 2006).
M. Xu et al., "Photoacoustic Imaging in Biomedicine", *Review of Scientific Instruments*, vol. 77, 041101 (Apr. 17, 2006).

* cited by examiner

OBJECT INFORMATION ACQUIRING APPARATUS AND CONTROL METHOD THEREFOR

BACKGROUND OF THE INVENTION

Field of the Invention

The present invention relates to an object information acquiring apparatus and a control method therefor.

Description of the Related Art

Researches for an optical imaging apparatus that irradiates light on an object such as a living organism from a light source such as a laser and converts information concerning the inside of the object obtained on the basis of the incident light into an image have been actively in progress in the medical field. As a kind of this optical imaging technique, there is photoacoustic imaging (PAI).

In the photoacoustic imaging, first, pulsed light from a light source is irradiated on an object. Then, an object tissue (a light absorber), which absorbs energy of the pulsed light propagated and diffused in the object, instantaneously expands and generates an acoustic wave. At this point, since an absorption ratio of the light energy is different depending on the type of the tissue and the wavelength of the light, there is a difference in a generated sound pressure between a test segment such as a tumor and the other tissues. Therefore, an information processing apparatus subjects an electric signal generated by receiving the acoustic wave in a probe to mathematic analysis processing, whereby it is possible to image object information. As the object information, an optical characteristic distribution in the object, in particular, an initial sound pressure distribution, an optical energy absorption density distribution, an absorption coefficient distribution, and the like are obtained. Further, it is possible to perform quantitative measurement of a specific substance concentration in the object, for example, oxygen saturation in blood on the basis of these kinds of information and information concerning the wavelength of irradiated light.

In recent years, a preclinical research for imaging a blood vessel image of a small animal using the photoacoustic imaging technique, and a clinical research for applying this principle to diagnosis of breast cancer and the like have been actively in progress ("Photoacoustic imaging in biomedicine", M. Xu, L. V. Wang, REVIEW OF SCIENTIFIC INSTRUMENT, 77, 041101, 2006). In the photoacoustic imaging, usually, an optical characteristic distribution of a light absorber present inside the object is converted into an image.

Non Patent Literature 1: "Photoacoustic imaging in biomedicine", M. Xu, L. V. Wang, REVIEW OF SCIENTIFIC INSTRUMENT, 77, 041101, 2006

SUMMARY OF THE INVENTION

However, deterioration sometimes occurs in a generated image because of a cause outside the object. For example, when a photoacoustic wave is reflected by an object holding member that holds the object, the reflected photoacoustic wave is also received by the probe. As a result, an electric signal including a component deriving from the reflected wave is used for image generation (image reconstruction) of the inside of the object. In an image generated in this way, artifacts due to the reflected wave occur and image deterioration occurs.

The present invention has been devised in view of the above problem and an object of the present invention is to, even if a reflected wave of a photoacoustic wave is received, reduce image deterioration due to the influence of the reflected wave in photoacoustic image formation.

The present invention provides an object information acquiring apparatus comprising:

a probe configured to detect a photoacoustic wave generated from an object irradiated with light;

a signal collector configured to generate a first detection signal from the photoacoustic wave;

a signal processor configured to generate, from the first detection signal, a second detection signal in which a component having a phase inverted from the phase of a component deriving from the photoacoustic wave is reduced, by using a differential signal of an impulse response of the probe; and an image generator configured to generate image data on the inside of the object using the second detection signal.

The present invention also provides a control method for an object information acquiring apparatus including a probe configured to detect a photoacoustic wave generated from an object irradiated with light, a signal collector, a signal processor, and an image generator, the control method comprising:

the signal collector generating a first detection signal from the photoacoustic wave;

the signal processor generating, from the first detection signal, a second detection signal in which a component having a phase inverted from the phase of a component deriving from the photoacoustic wave is reduced, by using a differential signal of an impulse response of the probe; and the image generator generating image data on the inside of the object using the second detection signal.

According to the present invention, in photoacoustic image formation, even if a reflected wave of a photoacoustic wave is received, it is possible to reduce image deterioration due to the influence of the reflected wave.

Further features of the present invention will become apparent from the following description of exemplary embodiments with reference to the attached drawings.

DESCRIPTION OF THE EMBODIMENTS

Figure 1:
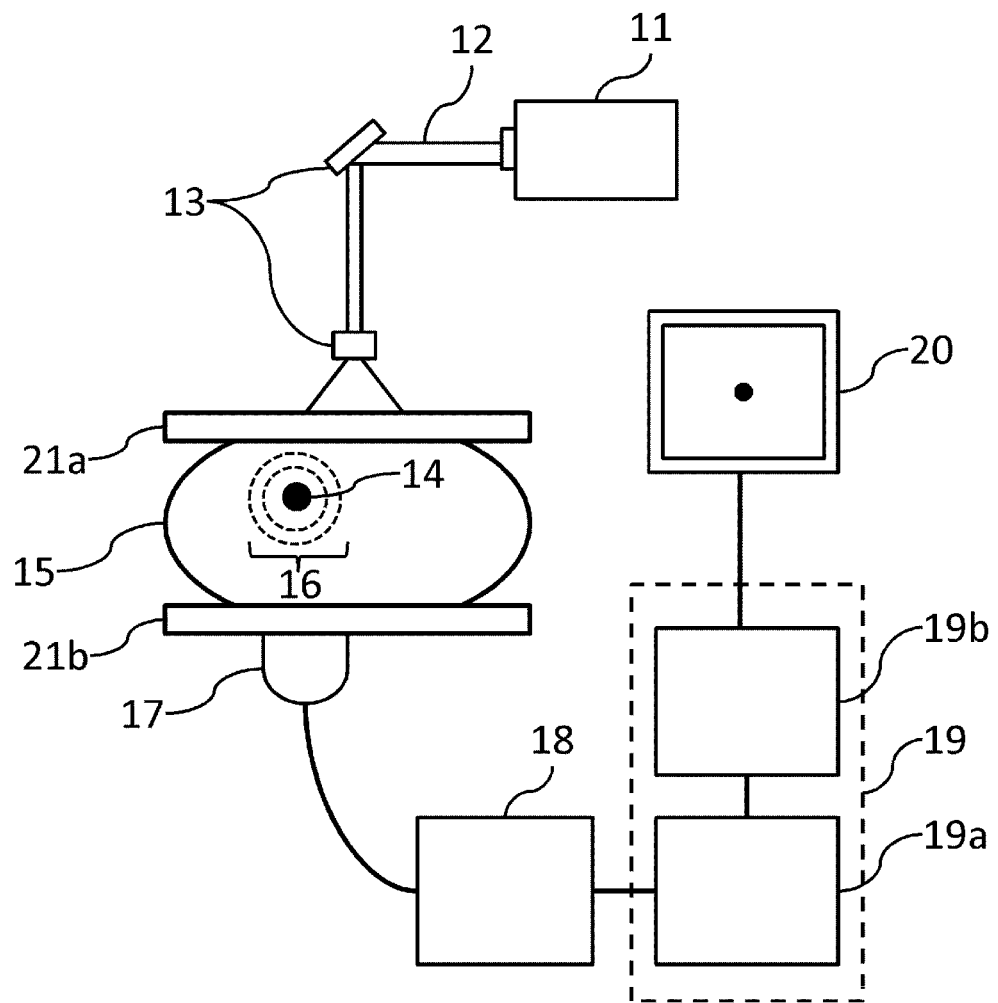
FIG. 1 is a diagram schematically showing an example of the configuration of a photoacoustic image-forming apparatus.

A preferred embodiment of the present invention is explained below with reference to the drawings. However, the dimensions, the materials, the shapes, a relative arrangement, and the like of components described blew should be changed as appropriate according to the configuration and various conditions of an apparatus applied with the invention and are not meant to limit the scope of the present invention to the description explained below.

In the present invention, an acoustic wave includes an elastic wave called sound wave, ultrasonic wave, photoacoustic wave, and optical ultrasonic wave. A receiver (a probe) receives the acoustic wave propagated through an object. An object information acquiring apparatus of the present invention is an apparatus that makes use of a photoacoustic effect of receiving an acoustic wave generated in an object by irradiating light (an electromagnetic wave) on the object and acquiring characteristic information in the object.

The characteristic information in the object acquired by the apparatus indicates object information that reflects an initial sound pressure of an acoustic wave caused by light irradiation, optical energy absorption density derived from the initial sound pressure, an absorption coefficient, the concentration of a substance forming a tissue, or the like. The concentration of the substance is, for example, oxygen saturation or oxygenated or reduced hemoglobin concentration. The characteristic information may be acquired as distribution information indicating characteristics in positions in the object rather than as numerical value data. That is, distribution information such as an absorption coefficient distribution or an oxygen saturation distribution may be acquired as image data.

In the following description, as an example of the object information acquiring apparatus, a photoacoustic image-forming apparatus that acquires characteristic information inside an object and converts the information into an image using photoacoustic tomography, which is a kind of photoacoustic imaging, is explained. A representative object is a breast of a living organism but is not limited to this. The present invention can also be grasped as a photoacoustic image-forming method by the photoacoustic image-forming apparatus or a control method for the apparatus.

Apparatus Configuration

The configuration of a photoacoustic image-forming apparatus according to this embodiment is explained with reference to FIG. 1. Note that, in the following description, in principle, the same components are denoted by the same reference numerals and signs and explanation of the components is omitted.

The photoacoustic image-forming apparatus in this embodiment includes, as basic components, a light source 11, an object holding member 21, a probe 17 functioning as a detector of an acoustic wave, and a signal processor 19. Pulsed light 12 emitted from the light source 11 is guided while being processed into a desired light distribution shape by an optical system 13 including a lens, a mirror, an optical fiber, and a diffuser and is irradiated on an object 15 such as a living organism. When a part of energy of light propagated through the inside of the object 15 is absorbed by a light absorber (resulting in a sound source) 14 such as a blood vessel, a photoacoustic wave 16 is generated by thermal expansion of the light absorber 14. A part of the generated photoacoustic wave 16 is received by the probe 17. At this point, a part of the photoacoustic wave 16 is made incident on the probe 17 after undergoing, for example, reflection by the object holding member 21 or the like. After being detected by the probe 17, the photoacoustic wave 16 and a reflected waver thereof are amplified or digitally converted by a signal collector 18, subjected to predetermined processing by the signal processor 19, and finally converted into image data (optical characteristic value information data) of the object, and displayed on a display device 20.

Light Source 11

The light source 11 irradiates light on an object. When the object is a living organism, the light source 11 irradiates light having a wavelength absorbed by a specific component in the object. In the present invention, a wavelength equal to or larger than 500 nm and equal to or smaller than 1200 nm is preferable such that light is propagated to the inside of the object. The light source 11 may be integrated with an apparatus main body or may be separated from the apparatus main body. As the light source 11, a pulsed light source capable of generating pulsed light in the order of several nanoseconds to several hundred nanoseconds is preferable. In order to efficiently generate a photoacoustic wave, pulse width of about 10 nanoseconds is particularly suitably used. As the light source 11, a laser from which a large output is obtained is preferable. However, a light emitting diode and the like can also be used. As the laser, various lasers such as a solid state laser, a gas laser, a fiber laser, a dye laser, and a semiconductor laser can be used. Timing, a waveform, intensity, and the like of irradiation are controlled by a not-shown light source controller.

Optical System 13

The optical system 13 guides the light 12 irradiated from the light source 11 to the object while processing the light 12 into a desired light distribution shape. The optical system 13 is typically configured by a lens, a mirror, a light diffuser, an optical waveguide such as an optical fiber, and the like. Note that it is preferable to spread the light to a certain degree of an area rather than condensing the light with a lens from a viewpoint that it is possible to increase safety for the object and a diagnosis region.

Object 15 and Light Absorber 14

The object 15 and the light absorber 14 are explained below, although not included in the apparatus of the present invention. Main objects of the photoacoustic image-forming apparatus of the present invention are diagnosis of a malignant tumor, a vascular disease, and the like of a human and an animal, follow-up of a chemical treatment, and the like. Therefore, as the object 15, a living organism, specifically, a target segment of diagnosis such as a breast, a finger, or a limb of a human body or an animal is assumed. As the light absorber 14 inside the object, a light absorber having a relatively high absorption coefficient in the object is assumed. For example, if a human body is a measurement target, oxygenated or reduced hemoglobin, a blood vessel including a lot of the oxygenated or reduced hemoglobin, or a malignant tumor including a lot of newborn blood vessels corresponds to the light absorber 14. A light absorber on the surface of the object is, for example, melanin near the surface of the skin.

Probe 17

The probe 17 is a detector configured to detect an acoustic wave generated on the surface and the inside of the object and convert the acoustic wave into an electric signal, which is an analog signal. The probe 17 may be any probe as long as the probe can detect the acoustic wave such as a transducer that makes use of a piezoelectric phenomenon, a transducer that makes use of resonance of light, or a transducer that makes use of a change in a capacity. By using, as the probe 17, a multidimensional array element in which a plurality of reception elements are one-dimensionally or two-dimensionally arranged, it is possible to simultaneously detect acoustic waves in a plurality of places. As a result, it is possible to reduce a detection time and reduce noise due to a body motion.

Signal Collector 18

The signal collector 18 amplifies an electric signal obtained by the probe 17 and performs conversion from an analog signal into a digital signal. The signal collector 18 is typically configured by an amplifier, an A/D converter, a field programmable gate array (FPGA) chip, and the like. When a plurality of detection signals are obtained from the probe 17, it is desirable that the signal collector 18 can simultaneously process a plurality of signals. Consequently, it is possible to reduce time until an image is formed. Note that, in this specification, a "detection signal" is a concept including both of an analog signal acquired from the probe 17 and a digital signal subjected to AD conversion thereafter. The detection signal is also referred to as "photoacoustic signal".

Signal Processor 19

The signal processor 19 acquires image data of the inside of the object through image reconstruction. Typically, a work station is used as the signal processor 19. Signal processing, image reconstruction processing, and the like are executed by a programmed computer program using an information processing device (a CPU, etc.) of the work station. In the example shown in FIG. 1, software used by the signal processor 19 includes a signal processing module 19a configured to perform processing for selectively reducing a phase-inverted reflected signal and an image reconstruction module 19b configured to generate image data. The signal collector 18 and the signal processor 19 are sometimes integrated. In this case, image data of the object can also be generated by hardware processing. The signal processing module 19a and the image reconstruction module 19b are respectively equivalent to a signal processor and an image generator of the present invention.

Display Device 20

The display device 20 displays image data output from the signal processor 19. For example, a liquid crystal display is used as the display device 20. Note that the display device 20 may be provided separately from the photoacoustic image-forming apparatus of the present invention.

Object Holding Member 21

The object holding member 21 holds the object. The object holding member 21 may include a member configured to hold liquid for matching the acoustic impedance of the object and the acoustic impedance of the probe. The object holding member or the holding member for the matching liquid is preferably transparent on a light passing side. For example, a plastic plate of polymethylpentene or acrylic, a glass plate, or the like is used as the object holding member or the holding member for the matching liquid. In general, since these members are harder than the living organism, the members have acoustic impedance larger than the acoustic impedance of the living organism. Therefore, as explained in detail below, when a photoacoustic wave is made incident on the object holding member 21 from the object 15, the phase of a reflected wave on an interface of the object holding member 21 is inverted 180°. As the shape of the object holding member, a tabular shape for holding the object is typically assumed. The object holding member is equivalent to a holding member of the present invention.

The probe 17 can also be considered as the object holding member 21. Usually, the acoustic impedance of a detection element (e.g., a PZT) of the probe is larger than the acoustic impedance of the object. Therefore, since the phase of a reflected wave of a photoacoustic wave made incident on the object from the probe is inverted 180°, it is possible to reduce the reflected light with the method of the present invention.

In FIG. 1, the object is held using two object holding members 21a and 21b. Consequently, the object is fixed not to move. The thickness of the object decreases and light can reach the object. In this specification, when it is unnecessary to distinguish the two object holding members 21a and 21b, the object holding members 21a and 21b are collectively described as the object holding member 21.

Photoacoustic Image-Forming Method

Processing performed by the signal processor 19, which is a characteristic of the present invention, is explained in detail with reference to FIGS. 2 to 6. In the following explanation, the photoacoustic wave 16 generated inside the object is multiply reflected on the object holding member 21 and a multiple reflected signal of the photoacoustic wave 16 is received by the probe 17. In this case, even when the multiple reflected signal is included in a signal from the object, with the photoacoustic imaging-forming method according to the present invention, it is possible to reduce artifacts due to the influence of the multiply reflection in a reconfigured image.

Mathematical Representation of Phase Inversion of an Acoustic Wave

Figure 3:
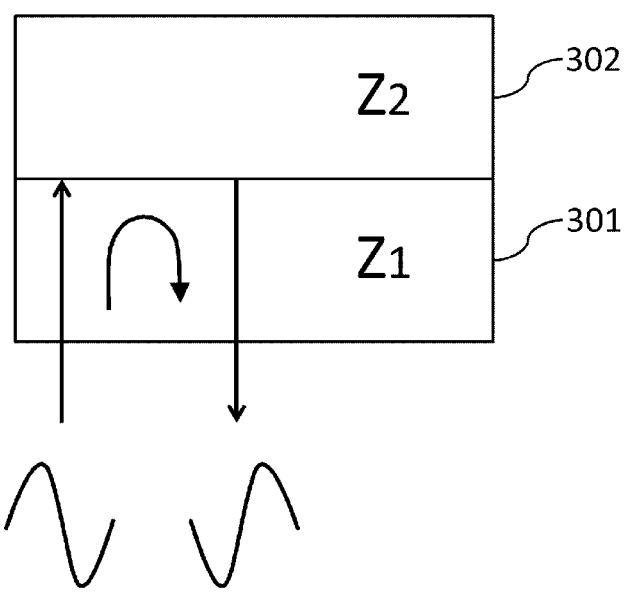
FIG. 3 is a schematic diagram showing an example in which the phase of a reflected wave is inverted with respect to an incident wave.

First, a physical phenomenon of reflection of an acoustic wave is explained as a precondition. In FIG. 3, the acoustic impedance (Z) of a region 301 is Z1 (Z=Z1) and the acoustic impedance of a region 302 is Z2 (Z=Z2). The acoustic impedance of the region 302 is relatively larger than the acoustic impedance of the region 301 (Z1<Z2). It is known that, when an acoustic wave is made incident on the region 302 from the region 301 in this situation, the phase of a reflected light on an interface between the region 301 and the region 302 is inverted 180°.

This phenomenon is applied to the object 15 and the object holding member 21 shown in FIG. 1 and examined. When the object 15 and the object holding member 21 are compared, usually, the latter having higher rigidity has higher acoustic impedance. Therefore, when the photoacoustic wave 16 generated inside the object is made incident on the object holding member 21, the phase of the photoacoustic wave reflected on an interface of the object holding member 21 changes 180° with respect to the incident wave. Therefore, for example, the shape of an acoustic wave formed at a single frequency is inverted as shown in FIG. 3.

When the phase of an incident wave, which is a normal photoacoustic wave, and the phase of a reflected wave of the incident wave are different by 180° because of such a physical phenomenon, it is possible to distinguish the normal photoacoustic wave and the reflected wave of the photoacoustic wave with the method of the present invention. The method is explained in detail below.

An equation describing propagation of a photoacoustic wave is a wave equation like Expression (1).

[Math 1]

$$\frac{\partial^2 p(r, t)}{\partial t^2} - v^2 \nabla^2 p(r, t) = \Gamma H_r(r) \frac{\partial H_t(t)}{\partial t} \quad (1)$$

where, p(r, t) represents a temporal change of a photoacoustic wave sound pressure in positions r, v represents sound velocity (fixed), Γ represents a Gruneisen coefficient, Hr(r) represents a light absorption density distribution, and Ht(t) represents an input pulse of light. H(r, t) is equal to Hr(r)·Ht(t).

In Expression (1), a solution of a Green's function, that is, a solution pδ(r, t) in a delta sound source and a delta pulse is represented by the following Expression (2). Note that this solution indicates a spherical wave that spreads in a spherical shape:

[Math 2]

$$p_\delta(r, t) = \frac{\delta(|r| - vt)}{4\pi|r|} \quad (2)$$

When this solution is integrated in a sound source of an entire space, a sound pressure p(r, t) detected in a certain position r is obtained. The sound pressure p(r, t) is represented by the following Expression (3):

[Math 3]

$$p(r, t) = \frac{\Gamma}{4\pi} \int \frac{\delta(|r - r'| - v(t - t'))}{|r - r'|} H_r(r') \frac{\partial}{\partial t} H_t(t') dr' dt' \quad (3)$$

When the light pulse Ht(t) is assumed to be a delta pulse, the above expression can be simplified as indicated by Expression (4):

[Math 4]

$$p(r, t) = \frac{\Gamma}{4\pi} \frac{\partial}{\partial t} \int_{|r-r'|=vt}^{\infty} \frac{H_r(r')}{|r - r'|} dr' \quad (4)$$

On the other hand, since an actually observed signal is affected by the probe, which is a detector, the signal is represented by convoluting the above expression with an impulse response Pimp(t) of the probe. Therefore, the signal can be represented as indicated by Expression (5). The impulse response is also called probe response and can be acquired as a waveform output by the probe upon reception of a delta pulse signal.

[Math 5]

$$p_d(r, t) = p_{imp}(t) \otimes \frac{\Gamma}{4\pi} \frac{\partial}{\partial t} \int_{|r-r'|=vt}^{\infty} \frac{H_r(r')}{|r - r'|} dr' \quad (5)$$

In this expression, a sign after Pimp(t) of the right side represents convolution. Since a differential operator ∂/∂t is a linear operator, the differential operator ∂/∂t can be caused to act on the impulse response Pimp(t). When the differential operator is caused to act on the impulse response Pimp(t), the following Expression (6) is obtained:

[Math 6]

$$p_d(r, t) = \frac{\partial}{\partial t} p_{imp}(t) \otimes \frac{\Gamma}{4\pi} \int_{|r-r'|=vt}^{\infty} \frac{H_r(r')}{|r - r'|} dr' \quad (6)$$

This is a mathematical representation of a detection signal received by the probe. In the right side of this expression, a term other than the differentiated impulse response means velocity potential. A component corresponding to a photoacoustic wave generated from a positive generated sound pressure is theoretically a positive value. That is, a velocity potential component corresponding to a normal photoacoustic wave generated from a light absorber having an absorption coefficient higher than an absorption coefficient in the periphery is positive.

Discrimination Method by a Differential Signal of the Impulse Response

Figure 4A:
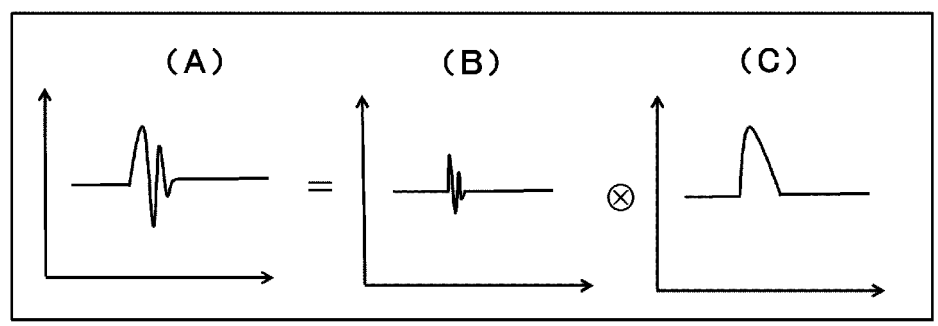
FIGS. 4A and 4B are schematic diagrams showing analysis examples of a photoacoustic wave.
Figure 4B:
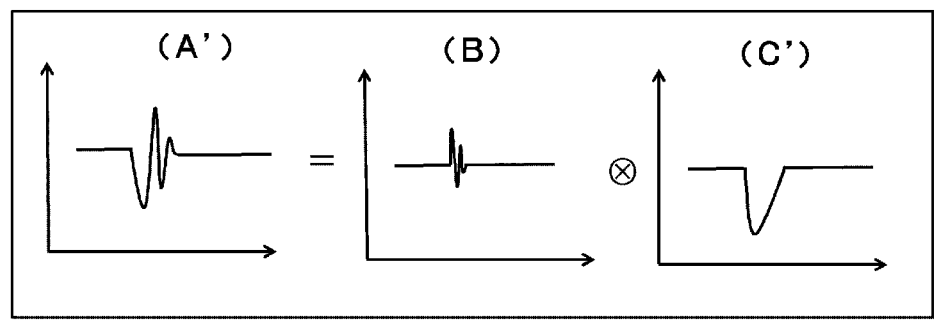

A difference between a normally received photoacoustic wave (incident wave) and a phase-inverted reflected photoacoustic wave is examined with reference to FIGS. 4A and 4B and Expression (6). FIG. 4A is a schematic diagram showing an example of an analysis of a "normal photoacoustic wave" the phase of which is not inverted by reflection or the like. FIG. 4B is a schematic diagram showing an example of an analysis of a reflected and phase-inverted photoacoustic wave of the "normal photoacoustic wave".

It is seen from Expression (6) that a reception signal (A) of the "normal photoacoustic wave" can be represented by convolution of differential (B) of the impulse response (i.e., an impulse response differential signal) and velocity potential (C) of a positive value. FIG. 4A schematically shows this state.

On the other hand, a reception signal (A') of the "photoacoustic wave phase-inverted by reflection" is convolution of the impulse response differential signal (B) and velocity potential (C') of a negative value. FIG. 4B schematically shows this state.

That is, the fact that the phase of a photoacoustic wave is inverted 180° by reflection is considered to be equivalent to the fact that the phase of velocity potential is inverted if a signal is separated from an impulse response differential signal. Therefore, by comparing values (positive and negative) of a velocity potential component obtained after the signal is separated by the impulse response differential signal, it is possible to distinguish the "normal photoacoustic wave" and the "photoacoustic wave phase-inverted by reflection".

It is seen from Expression (6) that the reception signal can be spectrally decomposed using the impulse response differential signal and converted into a spectrum signal, that is, velocity potential. Note that the spectral decomposition of the reception signal is equivalent to deconvoluting the reception signal with the impulse response differential signal or developing the reception signal with a base of the impulse response differential signal.

Typical Example of Phase Inversion

Figure 5A:
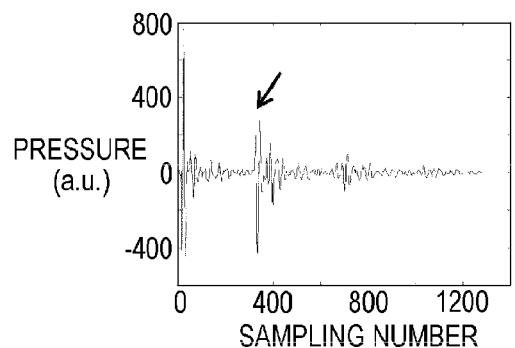
FIGS. 5A to 5E are schematic diagrams showing examples of spectral decomposition of a detection signal.

An example of spectral decomposition of a typical detection signal (a first detection signal) received by the photoacoustic image-forming apparatus shown in FIG. 1 is shown in FIGS. 5A to 5E. In FIGS. 5A to 5E, the ordinate represents the intensity of a sound pressure. The abscissa represents the number of times of sampling and corresponds to a detection time. FIG. 5A is an example of a reception signal output from the probe. The reception signal is represented as first detection signal. An arrow in FIG. 5A indicates a position of a reception signal deriving from a component phase-inverted by reflection on an interface between the object holding member 21 and the object 15 in the photoacoustic wave 16 generated by light irradiation on the surface of the probe.

Figure 5B:
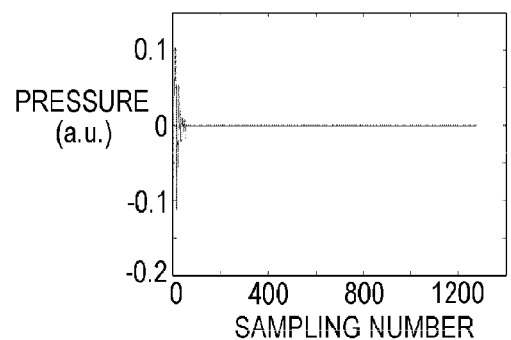
Figure 5C:
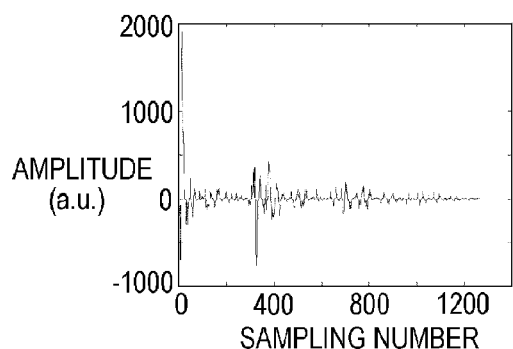
Figure 5D:
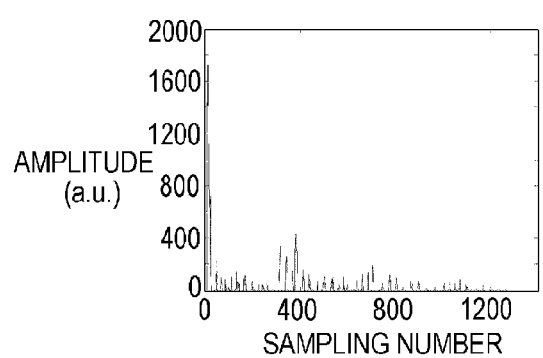
Figure 5E:
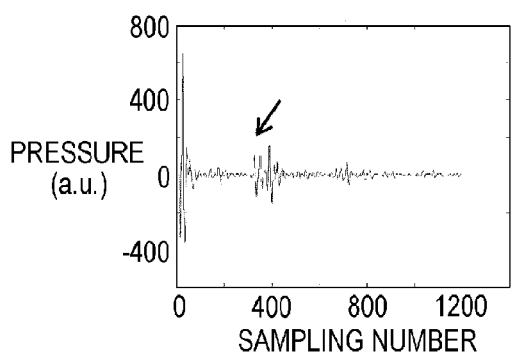

FIG. 5B is a signal obtained by time-differentiating an impulse response of the probe in use. A characteristic of the present invention resides in spectrally decomposing the first detection signal shown in FIG. 5A with the impulse response differential signal shown in FIG. 5B. A spectrum signal obtained by the spectral decomposition is shown in FIG. 5C. As shown in FIG. 5C, the spectrum signal, that is, a velocity potential component corresponding thereto includes positive and negative values. The negative value is mainly generated by a reflected wave, the phase of which is inverted 180°. FIGS. 5D and 5E are explained below.

Overview of Signal Processing

Figure 2:
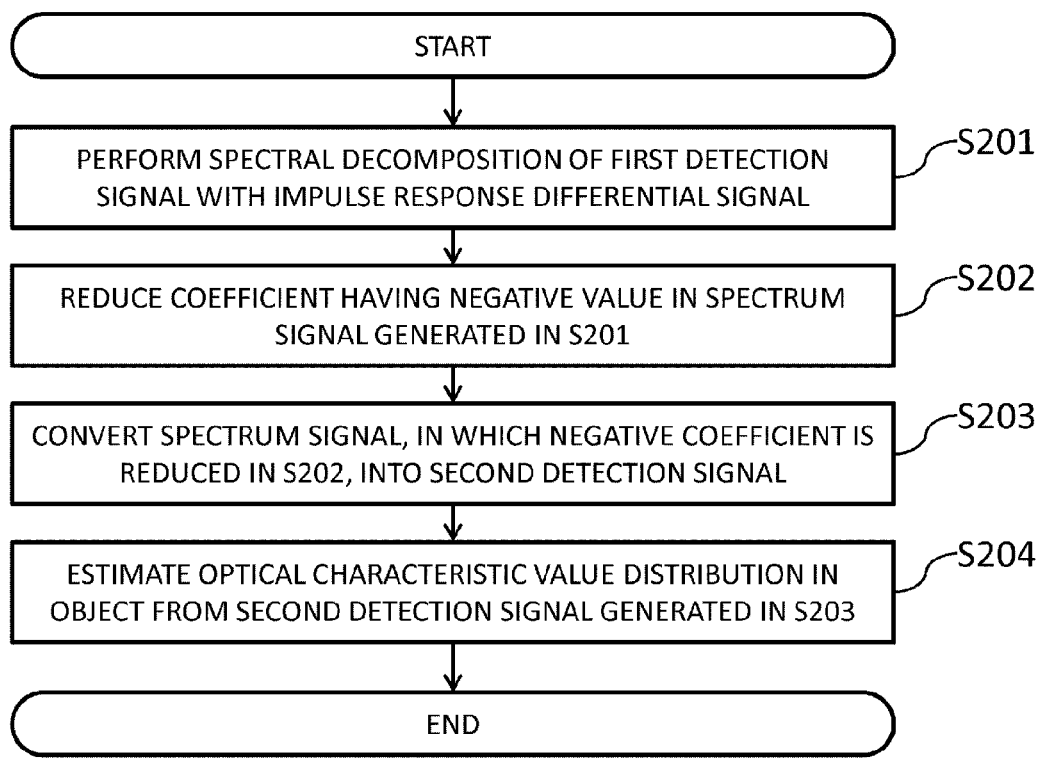
FIG. 2 is a flowchart for explaining an example of detection signal processing.

An overview of processing in the signal processor 19 is explained on the basis of the phenomenon that occurs during reflection of the acoustic wave with reference to a flowchart of FIG. 2.

[Processing 1] (Step S201): A Step of Spectrally Decomposing the First Detection Signal with the Impulse Response Differential Signal In this processing, as explained above, a spectrum signal is obtained by the spectral decomposition.

[Processing 2] (Step S202): A Step of Deleting a Coefficient of a Negative Value in the Spectrum Signal In this processing, a negative signal is selectively deleted in the spectrum signal shown in FIG. 5C. Since a coefficient after the spectrum decomposition is the same as the velocity potential as explained above, a negative value of the coefficient indicates a coefficient based on a photoacoustic signal, the phase of which is inverted by reflection. Therefore, by erasing the negative value, it is possible to delete a spectral component related to the photoacoustic signal, the phase of which is inverted by reflection. FIG. 5D is a spectrum signal in which the negative coefficient is reduced to zero.

[Processing 3] (Steps S203): A Step of Subjecting the Spectrum Signal Generated in the Processing 2 to Reconstruction Processing and Converting the Spectrum Signal into a Second Detection Signal Reconstruction processing for converting the spectrum signal, in which the negative coefficient is deleted in the processing 2, into a time signal is performed. As a method of the reconstruction processing, for example, there is a method of convoluting the spectrum signal with the impulse response differential signal or a method of base-converting the spectrum signal. Consequently, a second detection signal (a photoacoustic wave signal) with a reduced reflected signal, the phase of which is inverted 180°, can be generated. The second detection signal obtained by the processing is shown in FIG. 5E. An arrow in FIG. 5E indicates a position of a reception signal deriving from a component phase-inverted by interface reflection. When compared with FIG. 5A, it is seen that a value of the reception signal is greatly reduced.

As explained above, the spectral decomposition is performed using the impulse response differential signal, the negative value of the spectrum signal is reduced, and the spectrum signal is returned to a time domain. Consequently, it is possible to reduce only a reflected photoacoustic signal, the phase of which is inverted 180° with response to an impulse response.

[Processing 4] (Step S204): A Step of Estimating an Optical Characteristic Value Distribution of the Object Using the Second Detection Signal Subjected to the Reconstruction Processing in the Processing 3

An image reconstruction processing is performed using the second detection signal obtained in the processing 3 to estimate an optical characteristic value distribution of the object and form image data. Since the phase-inverted reflected photoacoustic wave is reduced in the second detection signal, it is possible to convert only the light absorber inside the object into image data and form a diagnosis image without image deterioration.

An image reconstruction method may be any method. For example, a back projection method in a time domain or a Fourier domain used in general photoacoustic tomography, a model base method (a repetitive reconstruction method), and the like can be applied. Note that, when the image reconstruction processing is unnecessary as in photoacoustic imaging in which a focus probe is used, digital detection signal data obtained in the processing 3 is directly converted into an image.

Example of a Reconfigured Image

Figure 6A:
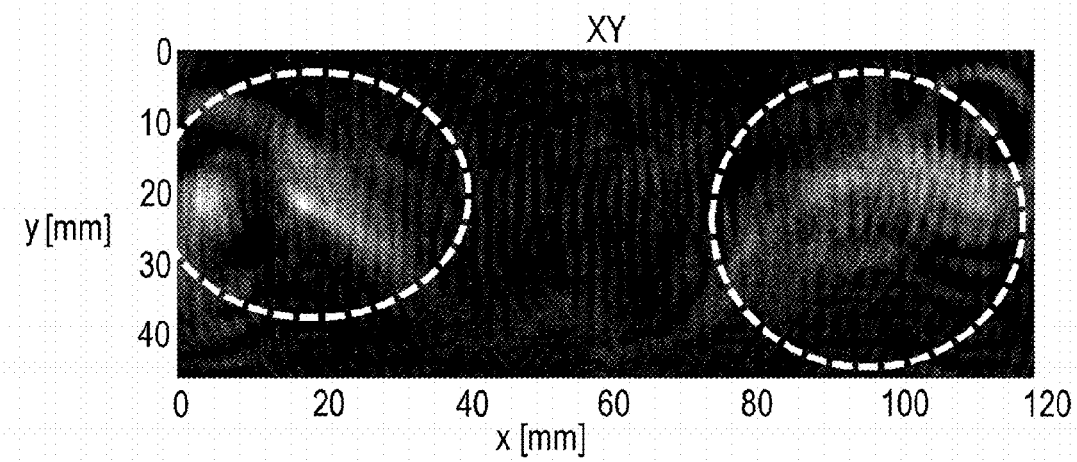
FIGS. 6A and 6B are images showing reconfigured initial sound pressure distributions.
Figure 6B:
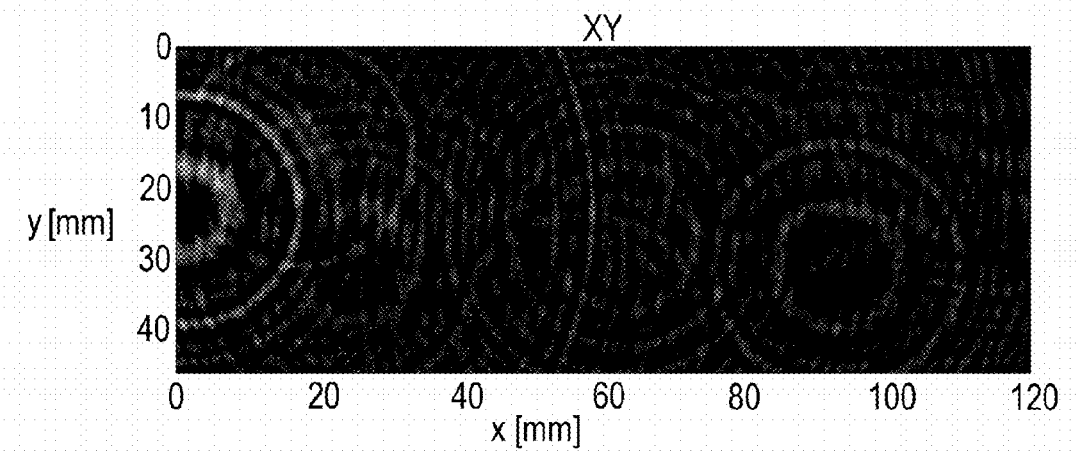

A reconfigured image obtained by the conventional method and a reconfigured image obtained by the method of the present invention are compared with reference to FIGS. 6A and 6B. The back projection method is used as a reconstruction method.

FIG. 6A is an example of an initial sound pressure distribution po obtained from a photoacoustic image in which a reflected signal is not reduced. That is, FIG. 6A is a reconfigured image obtained by using the first detection signal shown in FIG. 5A. In the figure, a black region indicates a region where a sound pressure is high. White regions indicate regions where the sound pressure is low. The white regions (in particular, regions surrounded by broken lines) are artifacts mainly due to the reflected signal and are unnecessary images.

FIG. 6B is an example of the initial sound pressure distribution po obtained from a photoacoustic signal in which the reflected signal is reduced. That is, FIG. 6B is a reconfigured image obtained by using the second detection signal in which the phase-inverted reflected signal is reduced as shown in FIG. 5E. It is seen that, compared with FIG. 6A, the artifacts due to the reflected signal are reduced and image deterioration due to the reflected photoacoustic signal is reduced.

Therefore, with the method of the present invention, it is possible to reduce image deterioration due to the influence of artifacts deriving from the reflected wave in the object holding member 21.

Note that, in this explanation, the suppression of the multiple reflection by the object holding member 21 is explained as an example. However, when not only the object holding member but also a member having acoustic impedance higher than the acoustic impedance of the object is in contact with the object, artifacts occur because of a reflected wave. The present invention can also be effectively applied to such artifacts.

Example 1

An example of the photoacoustic image-forming apparatus is explained. An apparatus configuration is the same as the apparatus configuration explained with reference to FIG. 1. In this example, a Ti:sa laser system utilizing double-wave YAG laser excitation was used as the light source 11. The laser system can irradiate light having wavelength of 700 to 900 nm. The irradiated laser light is irradiated on the object after being expanded to a radius of about 1 cm by the optical system 13 including a mirror and a beam expander. As the probe 17, a two-dimensional array type piezoelectric probe including 15×23 elements was used. The signal collector 18 has a function of simultaneously receiving all data of 345 ch from the probe 17, amplifying and digitally converting an analog signal, and then transferring the digital signal to a PC, which is the signal processor 19. The object 15 is a phantom simulating an object and is obtained by solidifying 1% of Intralipid and diluted ink using agar. In the phantom, a spherical object having a diameter of 2 mm colored by ink is embedded as the light absorber 14. As the object holding member 21 for holding the phantom, a flat phantom holding plate formed by polymethylpentene was arranged between the phantom 15 and the probe 17.

After setting of the phantom in the apparatus was completed, the light source irradiated light having a wavelength of 800 nm. The first detection signal is output through the detection by the probe and the processing by the signal collector. Subsequently, the signal processing module 19a spectrally decomposed the first detection signal obtained at that point using a signal obtained by differentiating an impulse response of the probe. The signal processing module 19a generated a spectrum signal through deconvolution by a differential impulse response of a reception signal. Further, the signal processing module 19a reduced a spectrum coefficient having a negative value in the spectrum signal to zero. By convoluting the differential impulse response with the spectrum signal in which the negative coefficient was reduced, the signal processing module 19a generated a signal (the second signal) with a phase-inverted reflected signal reduced with respect to the impulse response.

Thereafter, the image reconstruction module 19b performed the image reconstruction as in step S204 in FIG. 2 and calculated initial sound pressure distribution data. The back projection method was used. A reconfigured image obtained at that point was as shown in FIG. 6B. On the other hand, for comparison, a reconfigured image obtained from the first detection signal in which the reflected signal is not reduced was as shown in FIG. 6A.

FIGS. 6A and 6B are compared. As explained above, in FIG. 6A, the large artifacts (portions surrounded by the white broken lines) occur in places other than the actual light absorber because of the multiple reflection by the holding plate outside the object. On the other hand, in FIG. 6B, artifacts due to the multiple reflection signal are hardly seen. As a result, compared with FIG. 6A, an image corresponding to the light absorber inside the phantom was displayed more clearly.

As explained above, by selectively reducing the reflected photoacoustic signal phase-inverted by the reflection by the object holding member, it is possible to reduce artifacts in the reconfigured image.

Example 2

Figure 7:
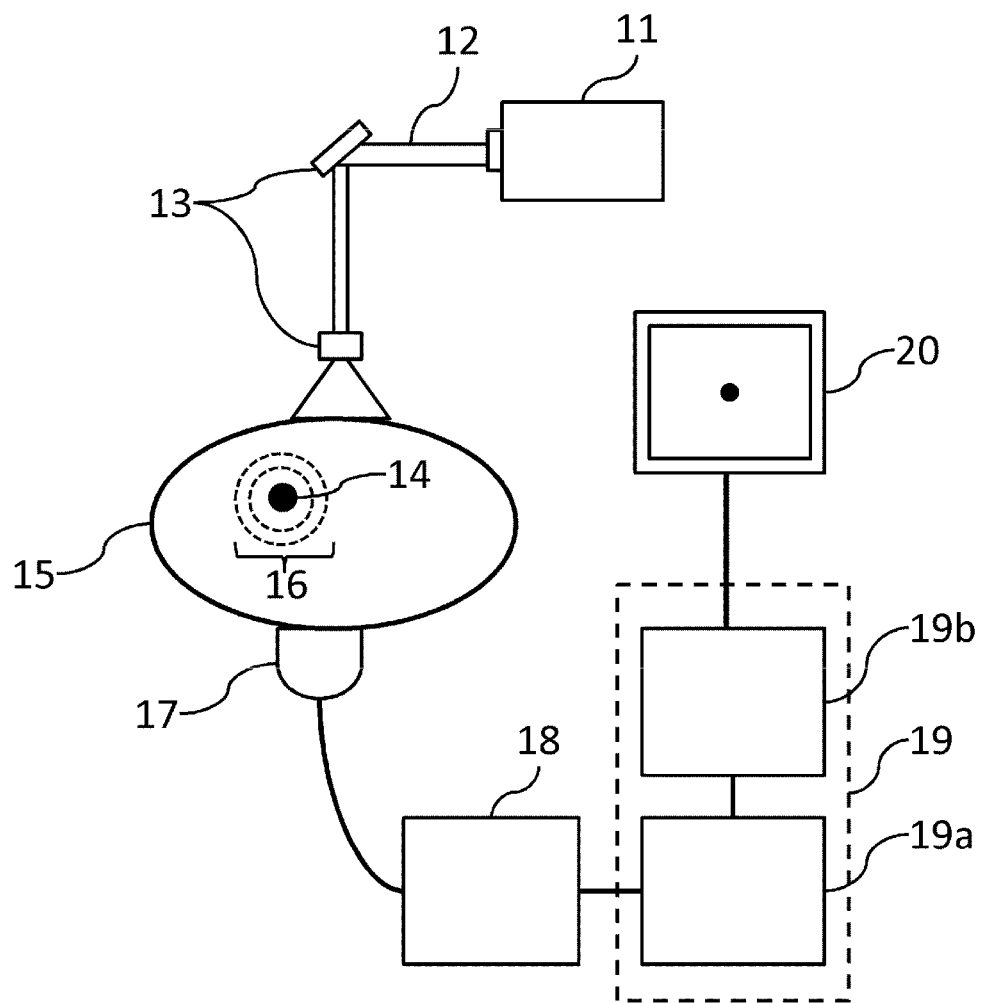
FIG. 7 is a diagram schematically showing an example of the configuration of the photoacoustic image-forming apparatus.

In an example 2, an example in which the probe 17 is used as the object holding member in the photoacoustic image-forming apparatus is explained with reference to FIG. 7. A difference from FIG. 1 is that the holding plate, which is the object holding member, is absent between the probe 17 and the object 15 and the probe is in direct contact with the object. As the object 15, a phantom same as the phantom in the example 1 is used.

After setting of the phantom in the apparatus was completed, the light source irradiated light having a wavelength of 800 nm. Subsequently, the signal processing module 19a selectively reduced, from the first detection signal obtained at that point, only a photoacoustic wave reflected on the interface between the probe and the phantom and phase-inverted. The signal processing module 19a performed spectral decomposition according to a basis expansion method with a differential impulse response signal set as a base. When coefficients of bases were calculated, assuming that a certain base was predominant, the signal processing module 19a calculated the coefficients with a constraint for making the coefficients sparse. Further, in a spectrum signal obtained by the spectral decomposition, the signal processing module 19a reduced a spectral coefficient having a negative value to zero. The signal processing module 19a base-converted the spectrum signal, in which the negative coefficient was deleted, into a time domain to thereby generate a signal obtained by reducing a reflected signal phase-inverted with respect to the impulse response. A reconfigured image obtained at that point was as shown in FIG. 6B. The artifacts due to the reflected signal were reduced. On the other hand, a reconfigured image obtained from a reception signal, in which a reflected signal was not reduced, was as shown in FIG. 6A. The artifacts due to the reflected signal were clearly confirmed.

As explained above, it is seen that, even when the probe is the object holding member, the artifacts due to reflection in the reconfigured image can be reduced by the method of the present invention.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., non-transitory computer-readable medium). Therefore, the computer (including the device such as a CPU or MPU), the method, the program (including a program code and a program product), and the non-transitory computer-readable medium recording the program are all included within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-030145, filed on Feb. 19, 2013, which is hereby incorporated by reference herein its entirety.

What is claimed is:

1. An object information acquiring apparatus comprising:
a signal processor configured to reduce, from a first signal obtained by detection of a photoacoustic wave generated from an object irradiated with light and a reflection wave of the photoacoustic wave with a probe, a component deriving from the reflection wave of the photoacoustic wave, by using a time-differential signal of an impulse response of the probe to generate a second signal; and
an image generator configured to generate image data by using the second signal,
wherein the signal processor is configured to generate a spectrum signal by performing spectral decomposition of the first signal using the time-differential signal of the impulse response,
wherein the spectral decomposition is performed by base conversion using the time-differential signal of the impulse response as a base or deconvolution using the time-differential signal of the impulse response,
wherein the signal processor is configured to reduce a negative coefficient of the spectrum signal, and
wherein the signal processor is configured to generate the second signal by converting the spectrum signal whose negative coefficient is reduced into a time signal, by base conversion using the time-differential signal of the impulse response as a base or convolution using the time-differential signal of the impulse response.

2. The object information acquiring apparatus according to claim 1, further comprising a holding member configured to hold the object, wherein the reflection wave is a wave reflected on the holding member.

3. The object information acquiring apparatus according to claim 2, wherein the reflection wave is a wave reflected on an interface between the object and the holding member.

4. The object information acquiring apparatus according to claim 2, wherein the holding member is a tabular member configured to hold the object.

5. The object information acquiring apparatus according to claim 2, wherein the probe also serves as the holding member.

6. The object information acquiring apparatus according to claim 1, wherein the impulse response is acquired as a waveform output by the probe which has received a delta pulse signal.

7. The object information acquiring apparatus according to claim 1, further comprising a display device configured to display the image data.

8. The object information acquiring apparatus according to claim 1, further comprising the probe configured to detect the photoacoustic wave generated from the object irradiated with light.

9. The object information acquiring apparatus according to claim 1, wherein the reflection wave is a wave having a phase inverted from a phase of the photoacoustic wave.

10. A method for generating image data on the basis of a first signal obtained by detection of a photoacoustic wave generated from an object irradiated with light with a probe, the method comprising:
generating a spectrum signal by performing spectral decomposition of the first signal using a time-differential signal of an impulse response of the probe, wherein the spectral decomposition is performed by base conversion using the time-differential signal of the impulse response as a base or deconvolution using the time-differential signal of the impulse response;
reducing a negative coefficient of the spectrum signal;
generating a second signal by converting the spectrum signal whose negative coefficient is reduced into a time signal as the second signal, by base conversion using the time-differential signal of the impulse response as the base or convolution using the time-differential signal of the impulse response; and
generating the image data by using the second signal.

11. A non-transitory computer-readable medium storing a computer program for causing an information processing device to execute the steps of the method according to claim 10.

* * * * *